US006596281B1

(12) United States Patent
Gennaro et al.

(10) Patent No.: US 6,596,281 B1
(45) Date of Patent: Jul. 22, 2003

(54) MYCOBACTERIUM TUBERCULOSIS SPECIFIC PROTEINS AND GENES, MIXTURES OF ANTIGENS AND USES THEREOF

(75) Inventors: Maria L. Gennaro, New York, NY (US); Konstantin P. Lyashchenko, Newark, NJ (US); Claudia M. A. Manca, New York, NY (US)

(73) Assignee: The Public Health Research Institute of the City of New York, Inc., Newark, NJ (US)

( * ) Notice: Subject to any disclaimer, the term of this patent is extended or adjusted under 35 U.S.C. 154(b) by 0 days.

(21) Appl. No.: 09/491,795

(22) Filed: Jan. 26, 2000

Related U.S. Application Data

(62) Division of application No. 08/796,792, filed on Feb. 6, 1997, now Pat. No. 6,087,163.
(60) Provisional application No. 60/011,364, filed on Feb. 9, 1996.

(51) Int. Cl.$^7$ .......................... A61K 39/04; A61K 39/38; A61K 39/02
(52) U.S. Cl. ...................... 424/248.1; 424/9.1; 424/9.2; 424/184.1; 424/234.1; 435/69.1; 435/253.1; 435/863; 530/300; 530/350
(58) Field of Search ...................... 424/9.1, 9.2, 184.1, 424/234.1, 248.1, 192.1; 435/69.1, 253.1, 863; 530/300, 350

(56) References Cited

U.S. PATENT DOCUMENTS 4,879,213 A 11/1989 Fox et al.

FOREIGN PATENT DOCUMENTS

WO WO 9605223 A1 * 2/1996 ........... C07K/14/35

OTHER PUBLICATIONS

Andersen & Brennan, "Proteins and Antigens of Mycobacteirum Tuberculosis," In Tuberculosis: Pathogenesis, Protection, and Control, Barry R. Bloom, ed., 1994 American Society for Microbiology, Washington, DC.
Andersen & Hansen, "Structure and Mapping of Antigenic Domains of Protein Antigen, b, a 38,000–Molecular–Weight Protein of Mycobacterium Tuberculosis," Infection and Immunity 57(8):2481–2488, 1989.
Andersen et al., "Proteins Released from Mycobacterium Tuberculosis during Growth," Infection and Immunity, 59(6):1905–1910, 1991.
Andersen et al., "T–Cell Proliferative Response to Antigens Secreted by Mycobacterium tuberculosis," Infection and Immunity 59(4):1558–1563, 1991.
Anderson & Heron, "Specificity of a Protective Memory Immune Response against Mycobacterium tuberculosis," Infection and Immunity, 61(3):844–851, 1993.
Ashbridge et al., "Nucleotide sequence of the 19 kDa antigen gene from Mycobacterium tuberculosis," Nuclei Acids Research 17(3):1249, 1989.
Bloch & Segal, "Viability and Multiplication of Vaccines in Immunization against Tuberculosis," Am. Rev. Tubercul. Pulm. Dis. 71:228–48, 1955.
Boesen et al., "Human T–Cell Responses to Secreted Antigen Fractions of Mycobacterium tuberculosis," Infection and Immunity 63(4):1491–1497, 1995.
Borremans et al., "Cloning, Sequence Determination, and Expression of a 32–Kilodalton–Protein Gene of Mycobacterium tuberculosis," Infection and Immunity 57(10):3123–3130, 1989.
Closs et al., "The Antigens of Mycobacterium bovis, Strain BCG, Studied by Crossed Immunoelectrophoresis: a Reference System," Scand. J. Immunol. 12:249–263, 1980.
Content et al., "The Genes Coding for the Antigen 85 Complexes of Mycobacterium tuberculosis and Mycobacterium bovis BCG Are Members . . . of M. tuberculosis," Infection and Immunity 59(9):3205–12, 1991.
Havlir et al., "Human Immune Response to Mycobacterium tuberculosis Antigens," Infection and Immunity 59(2):665–670, 1991.
Horwitz et al., "Protective immunity against tuberculosis induced by vaccination with major extracellular proteins of Mycobacterium tuberculosis," Proc. Natl. Acad. Sci. USA 92:1530–1534, 1995.
Hubbard et al., "Immunization of mice with mycobacterial culture filtrate proteins," Clin. Exp. Immunol. 87:94–98, 1992.
Laqueyrerie et al., "Cloning, Sequencing, and Expression of the apa Gene Coding for the Mycobacterium tuberculosis 45/47–Kilodalton Secreted Antigen Complex," Infection and Immunity 63(10):4003–4010, 1995.
Matsumoto et al., "Cloning and Sequencing of a Unique Antigen MPT70 from Mycobacterium tuberculosis H37Rv and Expression in BCG Using E. coli–Mycobacteria Shuttle Vector," Scand. J. Immunol. 41:281–287, 1995.
Matsuo et al., "Cloning and Expression of the Mycobacterium bovis BCG Gene for Extracellular α Antigen," Journal of Bacteriology, 170(9):3847–3854, 1988.
Nagai et al., "Isolation and Partial Characterization of Major Protein Antigens in the Culture Fluid of Mycobacterium tuberculosis," Infection and Immunity, 59(1):372–382, 1991.

(List continued on next page.)

Primary Examiner—Rodney P Swartz
(74) Attorney, Agent, or Firm—Fish & Richardson P.C.

(57) ABSTRACT

Two genes for proteins of *M. tuberculosis* have been sequenced. The DNAs and their encoded polypeptides can be used for immunoassays and vaccines.

Cocktails of at least three purified recombinant antigens, and cocktails of at least three DNAs encoding them can be used for improved assays and vaccines for bacterial pathogens and parasites.

11 Claims, 2 Drawing Sheets

OTHER PUBLICATIONS

Orme, "Induction of Nonspecific Acquired Resistance and Delayed–Type Hypersensitivity, but Not Specific Acquired Resistance . . . Vaccines," Infection and Immunity 56(12):3310–3312, 1988.

Orme et al., "T cell Response to Mycobacterium tuberculosis," J. of Infectious Diseases 167:1481–97, 1993.

Roberts et al., "Characteristics of protective immunity engendered by vaccination of mice with purified culture filtrate protein antigens of Mycobacterium tuberculosis," Immunology 85:502–508, 1995.

Sorensen et al., "Purification and Characterization of a Low–Molecular–Mass T–Cell Antigen Secreted by Mycobacterium tuberculosis," Infection and Immunity 63(5):1710–1717, 1995.

Yamaguchi et al., "Cloning and Characterization of the Gene for Immunogenic Protein MPB64 of Mycobacterium bovis BCG," Infection and Immunity 57(1):283–288, 1989.

Young et al., "Mycobacterial protein antigens: a compilation," Molecular Microbiology 6(2):133–145, 1992.

Wiker et al., "A localization index for distinction between extracellular and intracellular antigens of Mycobacterium tuberculosis," J. of General Microbiology 137:875–884, 1991.

Burgess et al., J. Cell Biol., 3:2129–2138, 1990.

Eiglmeier et al., Mol. Microbio. 7(2):197–206, 1993.

Lazar et al., Mol. Cell. Biol., 8(3):1247–1252, 1988.

Lowerie et al., Vaccine, 12(16):1537–40, 1994.

Manca et al., Infection and Immunity, 65(1):16–23, 1997.

Philipp et al., Proc. Natl. Acad. Sci 93:3132–3137, 1996.

Raitio et al., The EMBO Journal 6(9):2825–2833, 1987.

Yang et al., Proc. Natl. Acad. Sci. 87:9568–9572, 1990.

Genbank submission YOH3–MYCTU, submitted Sep. 1996, McLean et al.

Genbank submission P97175, submitted Jan. 1997, Oliver et al.

NCBI Sequence Database Entry, Accession No. P71697 (Jul. 15, 1998).

NCBI Sequence Database Entry, Accession No. Z80775 AL123456 (Jun. 24, 1999).

NCBI Sequence Database Entry, Accession No. P71697 (Feb. 15, 2000).

* cited by examiner

```
1    GTTCCTATCGAATCTGAGTTAGCAGCGGGTCATTTGCGGCTTAAGGTAATGACGTCGGCG           60

SD
61   AGGTTCGAACCAGGTAATCGCCCCAACAAGTAGTGGAGGTAGGGACCAATGAAGCTCACC          120
                                                        M  K  L  T

121  ACAATGATCAAGACGGCAGTAGCGGTCGTGGCCATGGCGGCCATCGCGACCTTTGCGGCA          180
     T  M  I  K  T  A  V  A  V  V  A  M* A  A  I  A  T  F  A  A

↓
181  CCGGTCGCGTTGGCTGCCTATCCCATCACCGGAAAACTTGGCAGTGAGCTAACGATGACC          240
     P  V  A  L  A  A  Y  P  I  T  G  K  L  G  S  E  L  T  M  T

241  GACACCGTTGGCCAAGTCGTGCTCGGCTGGAAGGTCAGTGATCTCAAATCCAGCACGGCA          300
     D  T  V  G  Q  V  V  L  G  W  K  V  S  D  L  K  S  S  T  A

301  GTCATCCCCGGCTATCCGGTGGCCGGCCAGGTCTGGGAGGCCACTGCCACGGTCAATGCG          360
     V  I  P  G  Y  P  V  A  G  Q  V  W  E  A  T  A  T  V  N  A

361  ATTCGCGGCAGCGTCACGCCCGCGGTCTCGCAGTTCAATGCCCGCACCGCCGACGGCATC          420
     I  R  G  S  V  T  P  A  V  S  Q  F  N  A  R  T  A  D  G  I

421  AACTACCGGGTGCTGTGGCAAGCCGCGGGCCCCGACACCATTAGCGGAGCCACTATCCCC          480
     N  Y  R  V  L  W  Q  A  A  G  P  D  T  I  S  G  A  T  I  P

481  CAAGGCGAACAATCGACCGGCAAAATCTACTTCGATGTCACCGGCCCATCGCCAACCATC          540
     Q  G  E  Q  S  T  G  K  I  Y  F  D  V  T  G  P  S  P  T  I

541  GTCGCGATGAACAACGGCATGGAGGATCTGCTGATTTGGGAGCCGTAGATCGTAGCTAAT          600
     V  A  M  N  N  G  M  E  D  L  L  I  W  E  P  *  (SEQ ID NO:2)

601  GCACGCCCAGGCGACCGCTGAGGTATTGGGCGCGGCAGGCTGGCGAGCCAGCTTCCCGCT
     GGTGGTGCGTGGAATGGCGCCG  682  (SEQ ID NO:1)
```

FIG. 1

```
                                     GGTACCGTGGCACGTCGGAGTCCGCGTC   28
GTCGGCACGGGGCACGCCGCCAGGCCCAGCGGTTGGCGATTCGGTCACGCCCAACAGGGT   88
ATAAGGGTGGCCCGGGAACCTCCGGGGCCGCGCTACCGGCCACGGGTTGGTCTCGGTTCC  148
GTTGCACCACGATCAGAGGTTCATTCCAGCTGCATTTCAAGCCTGTGCACTGCCATGGAG  208
                                                       SD
CGCTGGTTACATTCAGCCTCGACGACGGGCACCGTCGCCCGGCCATTCGGAGGGACCGAC  268
GCAAATGATCCAGATCGCGCGCACCTGGCGGGTCTTCGCAGGCGGCATGGCCACCGGTTT  328
     M  I  Q  I  A  R  T  W  R  V  F  A  G  G  M  A  T  G  F

CATCGGCGTGGTGCTGGTCACCGCCGGGAAGGCCTCAGCGGATCCCCTGCTGCCACCGCC  388
 I  G  V  V  L  V  T  A  G  K  A  S  A  D  P  L  L  P  P  P
                                       ↑
GCCTATCCCTGCCCCAGTCTCGGCGCCGGCAACAGTCCCGCCCGTGCAGAACCTCACGGC  448
 P  I  P  A  P  V  S  A  P  A  T  V  P  P  V  Q  N  L  T  A

GCTTCCGGGCGGGAGCAGCAACAGGTTCTCACCGGCGCCAGCACCCGCACCGATCGCGTC  508
 L  P  G  G  S  S  N  R  F  S  P  A  P  A  P  A  P  I  A  S

GCCGATTCCGGTCGGAGCACCCGGGTCCACCGCTGTGCCCCCGCTGCCGCCGCCAGTGAC  568
 P  I  P  V  G  A  P  G  S  T  A  V  P  P  L  P  P  P  V  T

TCCCGCGATCAGCGGCACACTTCGGGACCACCTCCGGGAGAAGGGCGTCAAGCTGGAGGC  628
 P  A  I  S  G  T  L  R  D  H  L  R  E  K  G  V  K  L  E  A

ACAGCGACCGCACGGATTCAAGGCGCTCGACATCACACTGCCCATGCCGCCGCGCTGGAC  688
 Q  R  P  H  G  F  K  A  L  D  I  T  L  P  M  P  P  R  W  T

TCAGGTGCCCGACCCCAACGTGCCCGACGCGTTCGTGGTGATCGCCGACCGGTTGGGCAA  748
 Q  V  P  D  P  N  V  P  D  A  F  V  V  I  A  D  R  L  G  N

CAGCGTCTACACGTCGAATGCGCAGCTGGTGGTGTATAGGCTGATCGGTGACTTCGATCC  808
 S  V  Y  T  S  N  A  Q  L  V  V  Y  R  L  I  G  D  F  D  P

CGCTGAGGCCATCACACACGGCTACATTGACAGCCAGAAATTGCTCGCATGGCAGACCAC  868
 A  E  A  I  T  H  G  Y  I  D  S  Q  K  L  L  A  W  Q  T  T

AAACGCCTCGATGGCCAATTTCGACGGCTTTCCGTCATCAATCATCGAGGGCACCTACCG  928
 N  A  S  M  A  N  F  D  G  F  P  S  S  I  I  E  G  T  Y  R

CGAAAACGACATGACCCTCAACACCTCCCGGCGCCACGTCATCGCCACCTCCGGAGCCGA  988
 E  N  D  M  T  L  N  T  S  R  R  H  V  I  A  T  S  G  A  D

CAAGTACCTGGTTTCGCTGTCGGTGACCACCGCGCTGTCGCAGGCGGTCACCGACGGGCC 1048
 K  Y  L  V  S  L  S  V  T  T  A  L  S  Q  A  V  T  D  G  P

GGCCACCGATGCGATTGTCAACGGATTCCAAGTGGTTGCGCATGCGGCGCCCGCTCAGGC 1108
 A  T  D  A  I  V  N  G  F  Q  V  V  A  H  A  A  P  A  Q  A

GCCTGCCCCGGCACCCGGTTCGGCACCGGTGGGACTACCCGGGCAGGCGCCTGGGTATCC 1168
 P  A  P  A  G  S  A  P  V  G  L  P  G  Q  A  P  G  Y  P

GCCCGCGGGCACCCTGACACCAGTCCCGCCGCGCTAGGTCGCGATGAGGCCGAGCAGAAA 1228
 P  A  G  T  L  T  P  V  P  P  R  *  (SEQ ID NO:4)

CACGGGCCCGCATGGAGCTCGGTGAGCGGATTCGTCGGCGGCCTCGTATGGTGAACGAAT 1288
GTTCCTCGCGGGTGTGCTGTGCATGTGTGCGGCGGCGGCGTCCGCCCTGTTCGGGAGCTG 1348
GTC 1351  (SEQ ID NO:3)
```

FIG. 2

SEQUENCE LISTING

<160> NUMBER OF SEQ ID NOS: 7

<210> SEQ ID NO 1
<211> LENGTH: 682
<212> TYPE: DNA
<213> ORGANISM: Mycobacterium tuberculosis
<220> FEATURE:
<221> NAME/KEY: CDS
<222> LOCATION: (109)...(585)

<400> SEQUENCE: 1

```
gttcctatcg aatctgagtt agcagcgggt catttgcggc ttaaggtaat gacgtcggcg        60
aggttcgaac caggtaatcg ccccaacaag tagtggaggt agggacca atg aag ctc       117
                                                     Met Lys Leu
                                                      1 acc aca atg atc aag acg gca gta gcg gtc gtg gcc atg gcg gcc atc       165
Thr Thr Met Ile Lys Thr Ala Val Ala Val Val Ala Met Ala Ala Ile
        5                  10                  15 gcg acc ttt gcg gca ccg gtc gcg ttg gct gcc tat ccc atc acc gga       213
Ala Thr Phe Ala Ala Pro Val Ala Leu Ala Ala Tyr Pro Ile Thr Gly
 20                  25                  30                  35 aaa ctt ggc agt gag cta acg atg acc gac acc gtt ggc caa gtc gtg       261
Lys Leu Gly Ser Glu Leu Thr Met Thr Asp Thr Val Gly Gln Val Val
                 40                  45                  50 ctc ggc tgg aag gtc agt gat ctc aaa tcc agc acg gca gtc atc ccc       309
Leu Gly Trp Lys Val Ser Asp Leu Lys Ser Ser Thr Ala Val Ile Pro
             55                  60                  65 ggc tat ccg gtg gcc ggc cag gtc tgg gag gcc act gcc acg gtc aat       357
Gly Tyr Pro Val Ala Gly Gln Val Trp Glu Ala Thr Ala Thr Val Asn
         70                  75                  80 gcg att cgc ggc agc gtc acg ccc gcg gtc tcg cag ttc aat gcc cgc       405
Ala Ile Arg Gly Ser Val Thr Pro Ala Val Ser Gln Phe Asn Ala Arg
     85                  90                  95 acc gcc gac ggc atc aac tac cgg gtg ctg tgg caa gcc gcg ggc ccc       453
Thr Ala Asp Gly Ile Asn Tyr Arg Val Leu Trp Gln Ala Ala Gly Pro
100                 105                 110                 115 gac acc att agc gga gcc act atc ccc caa ggc gaa caa tcg acc ggc       501
Asp Thr Ile Ser Gly Ala Thr Ile Pro Gln Gly Glu Gln Ser Thr Gly
                120                 125                 130 aaa atc tac ttc gat gtc acc ggc cca tcg cca acc atc gtc gcg atg       549
Lys Ile Tyr Phe Asp Val Thr Gly Pro Ser Pro Thr Ile Val Ala Met
            135                 140                 145 aac aac ggc atg gag gat ctg ctg att tgg gag ccg tagatcgtag            595
Asn Asn Gly Met Glu Asp Leu Leu Ile Trp Glu Pro
        150                 155 ctaatgcacg cccaggcgac cgctgaggta ttgggcgcgg caggctggcg agccagcttc      655
ccgctggtgg tgcgtggaat ggcgccg                                          682
```

<210> SEQ ID NO 2
<211> LENGTH: 159
<212> TYPE: PRT
<213> ORGANISM: Mycobacterium tuberculosis

<400> SEQUENCE: 2

```
Met Lys Leu Thr Thr Met Ile Lys Thr Ala Val Ala Val Val Ala Met
 1               5                  10                  15

Ala Ala Ile Ala Thr Phe Ala Ala Pro Val Ala Leu Ala Ala Tyr Pro
            20                  25                  30
```

```
Ile Thr Gly Lys Leu Gly Ser Glu Leu Thr Met Thr Asp Thr Val Gly
             35                  40                  45

Gln Val Val Leu Gly Trp Lys Val Ser Asp Leu Lys Ser Ser Thr Ala
         50                  55                  60

Val Ile Pro Gly Tyr Pro Val Ala Gly Gln Val Trp Glu Ala Thr Ala
 65                  70                  75                  80

Thr Val Asn Ala Ile Arg Gly Ser Val Thr Pro Ala Val Ser Gln Phe
                 85                  90                  95

Asn Ala Arg Thr Ala Asp Gly Ile Asn Tyr Arg Val Leu Trp Gln Ala
            100                 105                 110

Ala Gly Pro Asp Thr Ile Ser Gly Ala Thr Ile Pro Gln Gly Glu Gln
        115                 120                 125

Ser Thr Gly Lys Ile Tyr Phe Asp Val Thr Gly Pro Ser Pro Thr Ile
    130                 135                 140

Val Ala Met Asn Asn Gly Met Glu Asp Leu Leu Ile Trp Glu Pro
145                 150                 155

<210> SEQ ID NO 3
<211> LENGTH: 1351
<212> TYPE: DNA
<213> ORGANISM: Mycobacterium tuberculosis
<220> FEATURE:
<221> NAME/KEY: CDS
<222> LOCATION: (273)...(1202)

<400> SEQUENCE: 3
ggtaccgtgg cacgtcggag tccgcgtcgt cggcacgggg cacgccgcca ggcccagcgg      60
ttggcgattc ggtcacgccc aacagggtat aagggtggcc cgggaacctc cggggccgcg     120
ctaccggcca cgggttggtc tcggttccgt tgcaccacga tcagaggttc attccagctg     180
catttcaagc ctgtgcactg ccatggagcg ctggttacat tcagcctcga cgacgggcac     240
cgtcgcccgg ccattcggag ggaccgacgc aa atg atc cag atc gcg cgc acc      293
                                   Met Ile Gln Ile Ala Arg Thr
                                    1               5 tgg cgg gtc ttc gca ggc ggc atg gcc acc ggt ttc atc ggc gtg gtg      341
Trp Arg Val Phe Ala Gly Gly Met Ala Thr Gly Phe Ile Gly Val Val
         10                  15                  20 ctg gtc acc gcc ggg aag gcc tca gcg gat ccc ctg ctg cca ccg ccg      389
Leu Val Thr Ala Gly Lys Ala Ser Ala Asp Pro Leu Leu Pro Pro Pro
     25                  30                  35 cct atc cct gcc cca gtc tcg gcg ccg gca aca gtc ccg ccc gtg cag      437
Pro Ile Pro Ala Pro Val Ser Ala Pro Ala Thr Val Pro Pro Val Gln
 40                  45                  50                  55 aac ctc acg gcg ctt ccg ggc ggg agc agc aac agg ttc tca ccg gcg      485
Asn Leu Thr Ala Leu Pro Gly Gly Ser Ser Asn Arg Phe Ser Pro Ala
                 60                  65                  70 cca gca ccc gca ccg atc gcg tcg ccg att ccg gtc gga gca ccc ggg      533
Pro Ala Pro Ala Pro Ile Ala Ser Pro Ile Pro Val Gly Ala Pro Gly
             75                  80                  85 tcc acc gct gtg ccc ccg ctg ccg ccg cca gtg act ccc gcg atc agc      581
Ser Thr Ala Val Pro Pro Leu Pro Pro Pro Val Thr Pro Ala Ile Ser
         90                  95                 100 ggc aca ctt cgg gac cac ctc cgg gag aag ggc gtc aag ctg gag gca      629
Gly Thr Leu Arg Asp His Leu Arg Glu Lys Gly Val Lys Leu Glu Ala
    105                 110                 115 cag cga ccg cac gga ttc aag gcg ctc gac atc aca ctg ccc atg ccg      677
Gln Arg Pro His Gly Phe Lys Ala Leu Asp Ile Thr Leu Pro Met Pro
120                 125                 130                 135
```

```
ccg cgc tgg act cag gtg ccc gac ccc aac gtg ccc gac gcg ttc gtg    725
Pro Arg Trp Thr Gln Val Pro Asp Pro Asn Val Pro Asp Ala Phe Val
                140                 145                 150 gtg atc gcc gac cgg ttg ggc aac agc gtc tac acg tcg aat gcg cag    773
Val Ile Ala Asp Arg Leu Gly Asn Ser Val Tyr Thr Ser Asn Ala Gln
    155                 160                 165 ctg gtg gtg tat agg ctg atc ggt gac ttc gat ccc gct gag gcc atc    821
Leu Val Val Tyr Arg Leu Ile Gly Asp Phe Asp Pro Ala Glu Ala Ile
        170                 175                 180 aca cac ggc tac att gac agc cag aaa ttg ctc gca tgg cag acc aca    869
Thr His Gly Tyr Ile Asp Ser Gln Lys Leu Leu Ala Trp Gln Thr Thr
            185                 190                 195 aac gcc tcg atg gcc aat ttc gac ggc ttt ccg tca tca atc atc gag    917
Asn Ala Ser Met Ala Asn Phe Asp Gly Phe Pro Ser Ser Ile Ile Glu
200                 205                 210                 215 ggc acc tac cgc gaa aac gac atg acc ctc aac acc tcc cgg cgc cac    965
Gly Thr Tyr Arg Glu Asn Asp Met Thr Leu Asn Thr Ser Arg Arg His
                220                 225                 230 gtc atc gcc acc tcc gga gcc gac aag tac ctg gtt tcg ctg tcg gtg   1013
Val Ile Ala Thr Ser Gly Ala Asp Lys Tyr Leu Val Ser Leu Ser Val
                    235                 240                 245 acc acc gcg ctg tcg cag gcg gtc acc gac ggg ccg gcc acc gat gcg   1061
Thr Thr Ala Leu Ser Gln Ala Val Thr Asp Gly Pro Ala Thr Asp Ala
                250                 255                 260 att gtc aac gga ttc caa gtg gtt gcg cat gcg gcg ccc gct cag gcg   1109
Ile Val Asn Gly Phe Gln Val Val Ala His Ala Ala Pro Ala Gln Ala
265                 270                 275 cct gcc ccg gca ccc ggt tcg gca ccg gtg gga cta ccc ggg cag gcg   1157
Pro Ala Pro Ala Pro Gly Ser Ala Pro Val Gly Leu Pro Gly Gln Ala
280                 285                 290                 295 cct ggg tat ccg ccc gcg ggc acc ctg aca cca gtc ccg ccg cgc       1202
Pro Gly Tyr Pro Pro Ala Gly Thr Leu Thr Pro Val Pro Pro Arg
                300                 305                 310 taggtcgcga tgaggccgag cagaaacacg ggcccgcatg gagctcggtg agcggattcg   1262
tcggcggcct cgtatggtga acgaatgttc ctcgcgggtg tgctgtgcat gtgtgcggcg   1322
gcggcgtccg ccctgttcgg gagctggtc                                     1351

<210> SEQ ID NO 4
<211> LENGTH: 310
<212> TYPE: PRT
<213> ORGANISM: Mycobacterium tuberculosis

<400> SEQUENCE: 4

Met Ile Gln Ile Ala Arg Thr Trp Arg Val Phe Ala Gly Gly Met Ala
1               5                   10                  15

Thr Gly Phe Ile Gly Val Val Leu Val Thr Ala Gly Lys Ala Ser Ala
            20                  25                  30

Asp Pro Leu Pro Pro Pro Ile Pro Ala Pro Val Ser Ala Pro
        35                  40                  45

Ala Thr Val Pro Pro Val Gln Asn Leu Thr Ala Leu Pro Gly Gly Ser
    50                  55                  60

Ser Asn Arg Phe Ser Pro Ala Pro Ala Pro Ile Ala Ser Pro
65                  70                  75                  80

Ile Pro Val Gly Ala Pro Gly Ser Thr Ala Val Pro Pro Leu Pro Pro
                85                  90                  95

Pro Val Thr Pro Ala Ile Ser Gly Thr Leu Arg Asp His Leu Arg Glu
            100                 105                 110
```

-continued

```
Lys Gly Val Lys Leu Glu Ala Gln Arg Pro His Gly Phe Lys Ala Leu
        115                 120                 125
Asp Ile Thr Leu Pro Met Pro Pro Arg Trp Thr Gln Val Pro Asp Pro
130                 135                 140
Asn Val Pro Asp Ala Phe Val Val Ile Ala Asp Arg Leu Gly Asn Ser
145                 150                 155                 160
Val Tyr Thr Ser Asn Ala Gln Leu Val Val Tyr Arg Leu Ile Gly Asp
                165                 170                 175
Phe Asp Pro Ala Glu Ala Ile Thr His Gly Tyr Ile Asp Ser Gln Lys
                180                 185                 190
Leu Leu Ala Trp Gln Thr Thr Asn Ala Ser Met Ala Asn Phe Asp Gly
        195                 200                 205
Phe Pro Ser Ser Ile Ile Glu Gly Thr Tyr Arg Glu Asn Asp Met Thr
210                 215                 220
Leu Asn Thr Ser Arg Arg His Val Ile Ala Thr Ser Gly Ala Asp Lys
225                 230                 235                 240
Tyr Leu Val Ser Leu Ser Val Thr Thr Ala Leu Ser Gln Ala Val Thr
                245                 250                 255
Asp Gly Pro Ala Thr Asp Ala Ile Val Asn Gly Phe Gln Val Val Ala
                260                 265                 270
His Ala Ala Pro Ala Gln Ala Pro Ala Pro Ala Pro Gly Ser Ala Pro
        275                 280                 285
Val Gly Leu Pro Gly Gln Ala Pro Gly Tyr Pro Pro Ala Gly Thr Leu
        290                 295                 300
Thr Pro Val Pro Pro Arg
305                 310

<210> SEQ ID NO 5
<211> LENGTH: 5
<212> TYPE: PRT
<213> ORGANISM: Mycobacterium tuberculosis

<400> SEQUENCE: 5

Ala Tyr Pro Ile Thr
  1               5

<210> SEQ ID NO 6
<211> LENGTH: 5
<212> TYPE: DNA
<213> ORGANISM: Mycobacterium tuberculosis

<400> SEQUENCE: 6 ggagg                                                              5

<210> SEQ ID NO 7
<211> LENGTH: 20
<212> TYPE: PRT
<213> ORGANISM: Mycobacterium tuberculosis

<400> SEQUENCE: 7

Ala Tyr Pro Ile Thr Gly Lys Leu Gly Ser Glu Leu Thr Met Thr Asp
  1               5                  10                  15
Thr Val Gly Gln
            20
```

MYCOBACTERIUM TUBERCULOSIS SPECIFIC PROTEINS AND GENES, MIXTURES OF ANTIGENS AND USES THEREOF

This application is a divisional and claims priority of U.S. application Ser No. 08/796,792, filed Feb. 6. 1997, now U.S. Pat. No. 6,087,163 which claimed priority of provisional application No. 60/011,364, filed feb. 9, 1996.

This invention relates to *Mycobacterium tuberculosis*, other bacterial pathogens whose antigenicity is not caused by a single protein or component, and parasites, including detection thereof, diagnosis of infection and disease, and preparation of vaccines:

BACKGROUND

One of the important goals of research on *Mycobacterium tuberculosis*, the causative agent of tuberculosis (TB), is the identification of mycobacterial antigens that induce protective T-cell responses and/or stimulate humoral immunity during tubercular infection. Antigens in the former class constitute potential candidates for the development of effective vaccines, while those in the latter group can be tested as new, improved tools for diagnosis of TB.

Similarly, numerous other bacterial pathogens have pathogenicity that, as with TB, is not caused by a single protein, as is the case also with parasites generally. Antigens produced by these pathogens are also potential candidates for the development of effective vaccines.

Proteins that are actively secreted by *M. tuberculosis* have attracted considerable attention as potent immunogens. The observation that only live, dividing mycobacteria efficiently induce protective immunity (7, 22) led to the hypothesis that proteins that are actively secreted by *M. tuberculosis* during growth are key in generating protective T-cell responses (4, 23). Indeed, experimental vaccines based on culture filtrate proteins have been shown to induce some levels of protective immunity in animal models of. TB (5, 14, 15, 26). Secreted proteins of *M. tuberculosis* are also potent inducers of antibody production (13).

The identification and immunochemical characterization of individual components of *M. tuberculosis* culture filtrates is a crucial step toward understanding the role of the secreted proteins in inducing immune responses during the course of TB. More than 30 proteins are present in filtrates from short-term (4–5 day) cultures (3), prior to any substantial contamination of the filtrates by intracellular components released by autolysis of aging cells. Only about ten actively secreted proteins have been identified using antibodies from immunized animals (1); most of them have been characterized by gene cloning and nucleotide sequencing (2, 6, 9, 11, 17–20, 29, 34). Some of the known secreted proteins induce cellular immune responses (35); however, strong human T-cell responses to secreted protein fractions involve yet uncharacterized antigens in the cell filtrate (8, 29).

An aspect of this invention is an isolated DNA sequence encoding the amino acid sequence of the MPT63 antigen, a protein secreted by *M. tuberculosis*, that is specific for mycobacterial species that belong to the *M. tuberculosis* complex, as well as recombinant polypeptide sequences encoded by that DNA.

Another aspect of this invention is an isolated DNA sequence encoding the amino acid sequence of the MTC28 antigen, another protein secreted by *M. tuberculosis* that is similarly specific, as well as purified natural and/or recombinant polypeptide sequences encoded by that DNA.

Another aspect of this invention is a "cocktail" of purified natural and recombinant protein antigens or polypeptides for immunodiagnostics or vaccines, as well as DNA cocktails for vaccines.

Other aspects of this invention are in vitro and in vivo methods of detection of immune responses using the protein or polypeptide cocktails and DNA cocktails of this invention.

SUMMARY OF INVENTION

The gene for the protein MPT63 has been isolated and sequenced (SEQ ID NO:1). That gene can be incorporated into a plasmid and expressed in *E. coli* to produce purified MPT63 protein, whose sequence (SEQ ID NO:2) has been deduced. Additional expression systems will be apparent to persons skilled in the art.

The gene for the protein MTC28 has been isolated and sequenced (SEQ ID NO:3). That gene can be similarly expressed to produce purified MTC28 protein, whose sequence (SEQ ID NO:4) has been deduced.

Both MPT63 and MTC28 are proteins secreted by *M. tuberculosis*. Both are specific to the *M. tuberculosis* complex, which includes *M. tuberculosis, M. bovis, M. microti*, and *M. africanum*.

This invention includes the MPT63 amino acid sequence shown in FIG. 1 (SEQ ID NO:2) and the MTC28 amino acid sequence shown in FIG. 2 (SEQ ID NO:3). A preferred embodiment is the mature recombinant MPT63 protein which is the polypeptide extending from the A in the underlined AYPIT to the C-terminal P in FIG. 1, and the mature recombinant MTC28 protein which extends from the D following the underlined portion to the C-terminal R in FIG. 2. Also preferred are antigenic polypeptides derived from the sequences shown in FIG. 1 and FIG. 2, whether produced by natural, recombinant or synthetic (including chemical synthesis) means or other means known in the art. The invention also includes variants of these polypeptides that retain their antigenic and immunogenic properties.

This invention also includes vaccines that contain a recombinant MPT63 polypeptide or a recombinant MTC28 polypeptide. In preferred embodiments the vaccine includes either mature recombinant protein.

This invention includes a method of eliciting an immune response and/or protective immunity against *M. tuberculosis* or another member of the *M. tuberculosis* complex in a vertebrate, said method including administering to the vertebrate a recombinant MPT63 or MTC28 polypeptide, whereby said polypeptide elicits immune responses against the Mycobacterium in the vertebrate.

This invention includes an isolated nucleic acid having the sequence shown in FIG. 1 (SEQ ID NO:1) or FIG. 2 (SEQ ID NO:3). Other embodiments can be derived by making silent substitutions, those that do not change the amino acid sequence encoded by the nucleic acid, in the nucleic acid sequence. In preferred embodiments these nucleic acids are made by modifying the sequence by mutagenesis, recombination or synthetic (including chemical synthesis) means or other means known in the art. Also preferred are embodiments wherein the nucleic acid does not contain the entire nucleic acid sequence shown in FIG. 1 (SEQ ID NO:2) or FIG. 2 (SEQ ID NO:3), with or without silent substitutions.

A DNA vaccine according to this invention includes a vector, preferably a plasmid vector, and one or more isolated nucleotide sequences each encoding the MPT63, MTC28 polypeptide, and transcriptional and translational regulatory sequences operably linked to the isolated nucleotide sequences for expression in a cell of a vertebrate. The DNA vaccine may include the regulatory sequences of CMV immediate-early promoter and/or intron A, or other non-retroviral sequences.

This invention also includes methods of eliciting an immune response and/or protective immunity by administering to a vertebrate such a DNA vaccine, whereby expression of said nucleotide sequences in said cell elicits immune responses against the Mycobacterium.

In preferred methods of this invention the vertebrate is a human. A DNA vaccine according to this invention may be administered to a vertebrate through a route of administration selected from the group consisting of inhalation, intravenous, intramuscular, intraperitoneal, intradermal, and subcutaneous. A preferred embodiment is a method wherein the DNA vaccine is administered by contacting the DNA vaccine with a mucosal surface of the vertebrate. A preferred embodiment is a method wherein the DNA vaccine is microsphere encapsulated, and is administered by contacting the microsphere-encapsulated DNA vaccine with a mucosal surface of the vertebrate. A preferred embodiment is a method wherein the DNA vaccine is coated onto gold beads for administration to the vertebrate by particle bombardment delivery. A preferred embodiment is a method wherein the gold beads are approximately 1 pm to 2 pm in diameter. A preferred embodiment is a method wherein the protective immunity is homologous, homotypic, heterotypic, or heterologous.

This invention includes the use of mature MPT63 or MTC28 polypeptide or a fragment(s) thereof in diagnostic tests for the detection in a patient of an immune response to *M. tuberculosis* or another member of the *M. tuberculosis* complex. A diagnostic test can be performed in the format of the commonly used Mantoux or Tine test for the detection of an immune reaction in the skin. This invention also includes the use of mature MPT63 or MTC28 polypeptide, or a fragment(s) thereof, to bind antibody in human or animal sera in an ELISA, or any other solid-phase immunoassay. Several formats of solid-phase immunoassays are known in the art and can be adapted for use in this invention.

This invention includes the use of a nucleic acid sequence of this invention, as a probe for the detection of the *M. tuberculosis* complex. Nucleic acid detection assays are well known to those skilled in the art. Assays can involve direct or indirect detection of the target sequence. Amplification of the target sequence can also be performed prior to or as a part of detection.

Amplification can be performed with, ligase chain reaction, polymerase chain reaction, self-sustained sequence reaction, NASBA and Q-beta amplification. Specific primers for the amplification of the mpt63 gene or the mtc28 gene can be derived from the nucleic acid of the present invention by standard procedures (and tests for specificity). Such primers can be selected simply by testing 15 to 50 nucleotide long sequences derived from the gene for specific hybridization to and specific amplification of the gene in the presence of various nucleic acids expected to be present in a sample.

This invention includes mixtures of antigens, or antigen "cocktails", that include at least three and as many as six or even more *M. tuberculosis* antigens and/or peptides thereof, at least two of which and preferably all of which are specific to the *M. tuberculosis* complex. The mixture should preferably include at least two purified proteins or polypeptides that are highly immunologically active in an antibody system or in T-cell recognition, for use in serodiagnosis and skin tests, respectively.

Similar cocktails can be made of protein or polypeptide antigens expressed by other bacterial pathogens, such as Listeria, Shigella and Salmonella, or by parasites, such as Plasmodium, Leishmania and Trypanosoma.

This invention also includes vaccines, both protein-based and DNA-based. The vaccines may comprise cocktails of purified proteins or polypeptide antigens, of *M. tuberculosis* or another bacterial pathogen or a parasite. The vaccines may comprise cocktails of DNAs encoding such antigens. Each member of the cocktail must induce a protective immune response. For vaccines, specificity to the pathogen is not required. Preferably, the cocktail comprises the most protective antigens available.

Applications of the idea of antigen combinations for immunodiagnostics and vaccines include serodiagnosis by detection of a) specific antibodies in serum and/or in other body fluids against combinations of appropriate antigens; b) antibodies of different isotypes (IgM, IgG, IgA) combined in one test system, and specific to one antigen or to an antigen combination; c) specific antibodies and/or relevant antigen (s) present in immune complexes after immune complex dissociation, and d) free, pathogen-derived antigen(s). Free or immune complex-released antigens can be identified by using (a combination of) monoclonal antibodies. Applications also include delayed-type-hypersensitivity-based immunodiagnosis by measuring specific skin test reactivity and/or in vitro T cell proliferative responses (or cytokine production) using a mixture of purified proteins specific to the pathogen.

BRIEF DESCRIPTION OF THE DRAWINGS

FIG. 1 shows the nucleotide sequence (SEQ ID NO:1) of the gene encoding the MPT63 protein and the deduced amino acid sequence of the protein (SEQ ID NO:2).

FIG. 2 shows the nucleotide sequence (SEQ ID NO:3) of the gene encoding the MTC28 protein and the deduced amino acid sequence of the protein (SEQ ID NO:4).

DETAILED DESCRIPTION

FIG. 1 shows the nucleotide sequence (SEQ ID NO:1) of the gene encoding the MPT63 protein of *M. tuberculosis*. The sequence (SEQ ID NO:1) contains an open reading frame of 477 nucleotides that encodes the MPT63 protein, whose deduced amino acid sequence (SEQ ID NO:2) is also shown. The first codon (ATG) is shown in bold. The underlined pentapeptide (AYPIT)(SEQ ID NO:5) marks the start of the 130-aa mature protein; the proceeding 29 amino acid stretch constitutes the hydrophobic secretion signal peptide. The arrow indicates the cleavage site. A putative ribosomal binding site (GGAGG)(SEQ ID NO:6) is indicated. The deduced amino acid ("aa") sequence (SEQ ID NO:2) contains a pentapeptide (AYPIT) identical to the NH2-terminal sequence of the MPT63 protein purified from *M. tuberculosis* culture filtrates (21) and a 20-aa stretch (AYPIT GKLGS ELTMT DTVGQ)(SEQ ID NO:7) identical to the NH2-terminal sequence of a 16-Kda major extracellular protein of *M. tuberculosis* used in animal immunization studies (14). Because actively secreted proteins usually contain secretion signal peptides that are cleaved from the mature protein in the process of secretion (32), the AYPIT pentapeptide defined the NH2-terminus of the mature form of MPT63, a polypeptide of 130 aa having a calculated Mr of 13,655.

To localize the nucleotide sequence encoding the MPT63 protein in the *M. tuberculosis* genome, Southern blot analysis was performed using PvII-digested DNA from *M. tuberculosis* H37Rv and a non-radioactively labelled 378-bp NruI fragment internal to mpt63. A single band of approximately 5 kb was visualized after hybridization and chemiluminescence detection, indicating that the mpt63 gene is presumably present in a single copy in the bacterial chromosome. The same positive signal was detected using DNAs extracted from other reference strains (H37Ra, Erdman) and over thirty clinical isolates of *M. tuberculosis*, as well as from several isolates of *M. bovis* and *M. bovis* BCG. No restriction fragment length polymorphism was observed in DNAs that tested positive. In contrast, no hybridization signal was detected when DNAs extracted from unrelated mycobacterial species (*M. kansasii, M. smegmatis, M. hemophilus, M. avium*) were analyzed. These hybridization results suggest that the mpt63 gene is conserved in mycobacterial species of the *M. tuberculosis* complex, while it is absent in unrelated species (mycobacteria other than tuberculous, MOTT).

FIG. 2 shows the DNA sequence (SEQ ID NO:3) of the gene we have named mtc28 and the deduced amino acid sequence (SEQ ID NO:4) of the protein it encodes, the MTC28 antigen. Both proteins are specific for the *M. tuberculosis* complex in serology and in skin tests.

The nucleotide sequence (SEQ ID NO:3) contains a gene of 930 nucleotides. That gene encodes a full-length protein of 310 amino acids. Analysis of the deduced amino acid sequence (SEQ ID NO:4) indicates that the $NH_2$-terminal 32 amino acid residues have properties typical of hydrophobic secretion signal peptides. The putative cleavage site is indicated by an arrow. We have not yet purified MTC28 for *M. tuberculosis* for purposes of comparison.

Using techniques described above for mpt63, also mpt28 was found to be specific for the *M. tuberculosis* complex. In the case of mtc28, however, there is a restriction fragment length polymorphous associated with this gene in different strains of *M. tuberculosis* complex. Using the (rec) MTC28 and (rec) MPT63 proteins, we have been able to detect both humoral and T-cell mediate immune responses in animals infected with *M. tuberculosis*, in animals immunized with *M. bovis* BCG, and in TB patients.

Purified protein and polypeptide antigens can be made using all or part of the sequences shown in FIG. 1 (SEQ ID NO:1) and FIG. 2 (SEQ ID NO:3) by methods well known in the art. The cloning method we have used will be described for the mpt63 gene.

The DNA sequence shown in FIG. 1 (SEQ ID NO:1), and portions thereof, and the DNA sequence shown in FIG. 2 (SEQ ID NO:3), and portions thereof, can be obtained by methods well known in the art. *M. tuberculosis* genomic DNA and primers derived from FIG. 1 (SEQ ID NO:1) or FIG. 2 (SEQ ID NO:3) can be used to amplify the entire gene sequence or portions thereof by polymerase chain reaction amplification, for example. Libraries of *M. tuberculosis* genomic DNA and DNA probes derived from FIG. 1 (SEQ ID NO:1) and FIG. 2 (SEQ ID NO:3) can also be used to clone the mpt63 gene or portions thereof.

To obtain pure recombinant MPT63 protein in large amounts the sequence encoding the mature MPT63 protein (extending from nucleotide 196 to nucleotide 588, FIG. 1) was subcloned in the *E. coli* plasmid PQE-30 (Qiagene) as a fusion protein bearing a short polyhistidine tract at its NH2-terminus. The tagged protein, having an apparent molecular weight of 16–17 Kda was purified by affinity chromatography using nickel columns (25). The nickel-affinity purified terminally tagged protein is referred to as recombinant (rec) MPT63.

Native MPT63 purified from *M. tuberculosis* culture filtrates and (rec) MPT63 purified from *E. coli* were found to be immunologically indistinguishable. For example, double diffusion in gel using (rec) and native MPT63 as antigens and polyclonal antibodies raised against native MPT63 produced a reaction of complete identity. Also, using sera from guinea pigs infected with *M. tuberculosis*, levels of antibody to the recombinant and native MPT63 proteins were similar. Guinea pigs immunized with *M. bovis* BCG showed the same levels of skin reactivity to both proteins.

Since (rec) MPT63 has the same immunological properties as the native protein (and can be purified from *E. coli* cells under non-denaturing conditions, such that both linear and conformational epitopes are maintained), the recombinant product can be utilized for serological investigations of TB patients and to undertake studies on the role of this mycobacterial antigen in cellular immune responses during the course of TB without the limitations imposed by purification of the protein from *M. tuberculosis*. (Rec) MTC28 can be similarly used.

A "DNA transcription unit" is a polynucleotide sequence, bounded by an initiation site and a termination site, that is transcribed to produce a primary transcript. As used herein, a "DNA transcription unit" includes at least two components: (1) antigen-encoding DNA, and (2) a transcriptional promoter element or elements operatively linked for expression of the antigen coding DNA. Antigen-coding DNA can encode one or multiple antigens, such as antigens from two or more different Mycobacterial proteins. The DNA transcription unit can additionally be inserted into a vector which includes sequences for expression of the DNA transcription unit.

A DNA transcription unit can optionally include additional sequences such as enhancer elements, splicing signals, termination and polyadenylation signals, viral replicons, and bacterial plasmid sequences. In the present method, a DNA transcription unit (i.e., one type of transcription unit) can be administered individually or in combination with one or more other types of DNA transcription units.

DNA transcription units can be produced by a number of known methods. For example, DNA encoding the desired antigen can be inserted into an expression vector (see, for example, Sambrook et al., *Molecular Cloning, A Laboratory Manual*, 2d, Cold Spring Harbor Laboratory Press (1989)). With the availability of automated nucleic acid synthesis equipment, DNA can be synthesized directly when the nucleotide sequence is known, or by a combination of polymerase chain reaction (PCR), cloning, and fermentation. Moreover, when the sequence of the desired polypeptide is known, a suitable coding sequence for the polynucleotide can be inferred.

The DNA transcription unit can be administered to an individual, or inoculated, in the presence of adjuvants or other substances that have the capability of promoting DNA uptake or recruiting immune system cells to the site of the inoculation. It should be understood that the DNA transcription unit itself is expressed in the host cell by transcription factors provided by the host cell, or provided by a DNA transcription unit.

The desired antigen can be any antigen or combination of antigens from a Mycobacterium. The antigen or antigens can be naturally occurring, or can be mutated or specially modified. The antigen or antigens can represent different forms, such as strains of Mycobacteria. These antigens may or may not be structural components of a Mycobacterium. The encoded antigens can be translation products or polypeptides. The polypeptides can be of various lengths. In addition, they can be designated to undergo intracellular, extracellular, or cell-surface expression. Furthermore, they can be designed to undergo release from cells.

An individual can be inoculated through any parenteral route. For example, an individual can be inoculated by intravenous, intraperitoneal, intradermal, subcutaneous, inhalation, or intramuscular routes, or by particle bombardment using a gene gun. Muscle is a useful site for the delivery and expression of DNA transcription unit-encoding polynucleotide, because animals have a proportionately large muscle mass which is conveniently accessed by direct injection through the skin. A comparatively large dose of polynucleotide can be deposited into muscle by multiple and/or repetitive injections, for example, to extend immunization over long periods of time. Muscle cells are injected with polynucleotide encoding polypeptides, and these polypeptides are presented by muscle cells in the context of antigens of the major histocompatibility complex to provoke a selected immune response (see, e.g., Felgner, et al. WO90/11092, herein incorporated by reference).

The epidermis is another useful site for the delivery and expression of polynucleotide, because it is conveniently accessed by direct injection or particle bombardment. A comparatively large dose of polynucleotide can be deposited in the epidermis by multiple injections or bombardments to extend therapy over long periods of time. In immunization strategies of the invention, skin cells are injected with polynucleotide coding for antigenic or immunogenic polypeptides, and these polypeptides are presented by skin cells in the context of antigens of the major histocompatibility complex to provoke a selected immune response against the immunogen.

In addition, an individual can be inoculated by a mucosal route. The DNA transcription unit can be administered to a mucosal surface by a variety of methods including DNA-containing nose-drops, inhalants, suppositories, microsphere encapsulated DNA, or by bombardment with DNA coated gold particles. For example, the DNA transcription unit can be administered to a respiratory mucosal surface, such as the nares or the trachea.

Any appropriate physiologically compatible medium, such as saline for injection, or gold particles for particle bombardment, is suitable for introducing the DNA transcription unit into an individual.

Intradermal administration of DNA by particle bombardment can be used to deliver DNA for expression of a *M. tuberculosis* MPT63 and/or MTC28 polypeptide in skin cells. The Accell particle bombardment device ("gene gun"; Agracetus, Middleton, Wis. can employed to deliver DNA-coated gold beads to the epidermis.

Plasmid DNA can be affixed to gold particles by adding 10 mg of 0.95 pm gold powder (Degussa, South Plainfield, N.J.), and an appropriate amount of plasmid DNA, to a 1.5-ml centrifuge tube containing 50 pl of 0.1 M spermidine. Plasmid DNA and gold particles can be co-precipitated by the addition of 50 pl of 2.5 M $CaCl_2$ during vortex mixing, after which the precipitate is allowed to settle and is washed with absolute ethanol and resuspended in 2.0 ml of ethanol. The gold/DNA suspension can be transferred to a capped vial and immersed in a sonicating water bath for 2–5 seconds to resolve clumps. The 163 pl of the gold/DNA suspension is layered onto 1.8 cm×1.8 cm Mylar sheets and allowed to settle for several minutes after which the meniscus is broken and excess ethanol is removed by aspiration. Gold/DNA-coated mylar sheets are dried and stored under vacuum. The total amount of DNA per sheet is a function of the DNA/gold ratio and should range from 0.2 to 0.0002 ~g per sheet.

Vertebrates are anesthetized with a topical anesthetic. Abdominal target areas are shaved and treated with Nair (CarterWallace, N.Y.) for two minutes to remove residual stubble and stratum corneum. Target areas are thoroughly rinsed with water prior to gene delivery. DNA-coated gold particles are delivered into abdominal skin with the Accell instrument, which employs an electric spark discharge as the motive force. Each vertebrate should receive two nonoverlapping deliveries per immunization, at a discharge voltage of about 17 Kv. Particle bombardment technology is presented in the following articles, hereiri incorporated by reference: Yang, M. S. et al., (1990) Proc. Natl. Acad. Sci. USA 87:9568–9572; Yang N.-S. (1992) CRC Crit. Rev. Biotechnol. 12:335–356; and Cheng, L. et al. (1993) Proc. Natl. Acad. Sci. USA 90:4455–4459.

The beads deliver DNA into cells, where the DNA dissolves and can be expressed (Yang, M. S. et al. (1991) Proc. Natl. Acad. Sci. USA 88: 2726–2730). Expression is transient, with most of the expression being lost within 2–3 days due to the normal sloughing of the epidermis (Williams, R. S. et al., Proc. Natl. Acad. Sci. USA 88: 2726–2730 (1991)).

These particle bombardment techniques can be easily adapted for use in human patients using *M. tuberculosis* MPT63 and MTC28 DNA vaccines. Administration of a DNA vaccine to a human can be performed by any one or more of several routes selected from the following: intravenous, intramuscular, intraperitoneal, intradermal, inhalation, and subcutaneous. For example, intradermal administration by gene gun is a preferred route. The site of administration is chosen for the convenience of the patient. The dose is between 1 and 50 pg of DNA vaccine per kg body weight, preferably 10–25 ~g per kg body weight. For a human infant, two inoculations are given at a 4 week interval. A human of any age who is caring for an infected infant or is immunocompromised due to illness, drug treatment, or other cause putting him or her at risk of infection is inoculated with the DNA vaccine by gene gun delivery for at least 2 inoculations at 4 week intervals.

Mucosal routes of DNA inoculation involve the administration of microsphere-encapsulated DNA to raise protective responses against a *M. tuberculosis* challenge. MPT63 DNA vaccines can be encapsulated in microspheres. Each patient receives a primary inoculation and a boost. The patients receive approximately 1–50 ~g/kg body weight of microsphere-encapsulated DNA for both the primary and boost inoculations. Each administration of encapsulated DNA is delivered in 100 p1 of water intranasally.

A safe, effective vaccine that protects against infection by Mycobacterium is important in both human and veterinary medicine. A Mycobacterium DNA vaccine of the invention is useful in providing protection against Mycobacterium infection humans, human infants, caretakers of infected infants, and immunocompromised humans. A bovine and porcine DNA vaccines of the invention are useful to prevent Mycobacterium infections in cattle and piglets thereby allowing the animals to thrive for increased agricultural benefit. A DNA vaccine against any human or animal Mycobacterium can be constructed and used according to the invention. Such vaccines are useful in providing homologous protection against a specific strain of Mycobacterium. The DNA vaccine of the invention is also useful in providing heterologous protection in that a DNA vaccine derived from one species-specific Mycobacterium, serotype, or strain can be used to induce protective immunity against a Mycobacterium from a different species-specific Mycobacterium, serotype, or strain.

Broad protection against multiple strains within a given serotype is possible according to the invention by inoculating the human or animal with a DNA vaccine encoding a protection inducing protein from a Mycobacterium strain of the same serotype. Thus, a single DNA vaccine of the invention is useful in providing protection against multiple strains of Mycobacterium.

The recombinant MPT63 and MTC28 proteins, as well as polypetide portions thereof which are immunogenic or can be made immunogenic by techniques known in the art, are useful as components of a protein-based or subnit vaccine. Preparation and administration of such vaccines are well known in the art.

This invention also includes combinations, or "cocktails" of purified protein and polypeptide antigens or DNAs encoding them, and the use of such cocktails for immunodiagnostics and vaccines. Cocktails according to the invention include antigens (and DNAS) of bacterial pathogens whose pathogenicity (unlike, for example, cholera) is not primarily caused by a single protein or virulence factor, and of parasites generally. Preparation and use of cocktails are described below as exemplified by antigens (and DNAS) produced by *M. tuberculosis.*

For immunodiagnostics, including serodiagnosis and skin tests, the cocktail comprises at least three and as many as six or even more antigens (or their DNAS) that are specific to the pathogen, for example, the *M. tuberculosis* complex. Preferably, the antigens (proteins or polypeptides) are highly active in the immune responses measured by the test being employed. The cocktail includes at least two highly active antigens. As previously stated, both (rec) MPT63 and (rec) MTC28 are specific for the *M. tuberculosis* complex. In addition, both are highly active in skin tests, and MTC28 is highly active in serum antibody tests. We have tested, along with MPT63 and MTC28, a number of known protein antigens of *M. tuberculosis* in serodiagnosis and skin tests. DNA sequences encoding them are shown in FIGS. 1 and 2.

DNA sequences encoding additional protein antigens of *M. tuberculosis* are known in the art, and accordingly, recombinant versions of them can be made by standard cloning techniques, including the incorporation of appropriate transcription and translation signals. If a particular protein is non-specific, it is often the case that an epitope portion of the protein is specific. That can be determined by routine screening.

Routine experimentation is used to adjust the proportions of antigens in a particular cocktail. Levels of antibody response to different antigens and the plate-coating capacity of different antigens both vary. The same immunoassay may test for a combination of different Ig isotypes, including IgM, IgG and IgA, which may improve sensitivity of the test.

Tables 1 and 2 present the results of ELISAs for *M. tuberculosis* individual antigens and culture filtrates. In serodiagnosis, several of the antigens made by cloning published DNA sequences are specific to *M. tuberculosis* complex, namely, ESAT-6, MPT64, 38 kDa and 80 kDa. Several are considered highly reactive in the test, namely, ESAT-6, 14 kDa, 19 kDa, MPT64 and 38kDa. Table 1 presents ELISA results for serum IgG antibodies to *M. tuberculosis* from patients with active tuberculosis ("Active TB") and in asymptomatic individuals who were PPD positive ("PPD+"). ELISA plates were: coated using 1 μg/ml of purified mycobacterial protein or 4 μg/ml of *M. tuberculosis* culture filtrate ("M.tb.CF"). Sera were diluted 1:100. Results are expressed as O.D.L. (test sample $OD_{405}$ divided by mean $OD_{405}$ of five healthy PPD). Several responses above 2.00 were obtained in patients with active TB, and several responses above 1.60 were obtained in asymptomatic $PPD^+$ individuals. Table 1 illustrates that no single protein antigen, not even if specific for the pathogen, is highly involved in antibody responses in all cases of infection.

Table 2 presents ELISA results for serum IgG antibodies to *M. tuberculosis* from guinea pigs aerosol-infected with *M. tuberculosis*. The plates were prepared as described above, and sera were similarly diluted. Results are presented as $OD_{405}$. Table 2 is another illustration of the point made by Table 1.

TABLE 1

| Serum | ESAT-6 | 14 kDa | MPT63 | 19 kDa | MPT64 | MPT51 | MTC28 | 38 kDa | 45/47 kDa | 80 kDa | M.tb.CF |
|---|---|---|---|---|---|---|---|---|---|---|---|
| Active TB | | | | | | | | | | | |
| U-5 | 1.27 | 1.39 | 1.23 | 1.21 | 1.63 | 1.44 | 1.26 | 1.15 | 2.26 | 1.21 | 1.06 |
| U-8 | 1.10 | 1.05 | 1.12 | 1.50 | 1.60 | 2.78 | 1.10 | 2.32 | 1.45 | 1.17 | 2.65 |
| U-9 | 5.86 | 0.98 | 1.03 | 0.83 | 2.01 | 1.05 | 1.10 | 1.24 | 1.38 | 1.10 | 1.07 |
| B-4 | 2.49 | 1.44 | 1.80 | 1.26 | 1.91 | 1.83 | 1.26 | 2.21 | 1.57 | 1.60 | 1.12 |
| B-56 | 1.28 | 1.04 | 0.88 | 5.60 | 1.25 | 1.28 | 1.07 | 1.32 | .088 | .095 | 2.33 |
| B-120 | 0.95 | 1.22 | 0.87 | 1.38 | 1.24 | 0.95 | 1.03 | 0.80 | 0.80 | 1.02 | 3.29 |
| PPD+ | | | | | | | | | | | |
| U-10 | 0.83 | 1.36 | 1.16 | 0.83 | 1.78 | 1.29 | 0.88 | 1.60 | 1.79 | 1.10 | 1.07 |
| U-11 | 0.80 | 1.71 | 0.96 | 1.06 | 1.52 | 1.40 | 0.94 | 1.24 | 1.41 | 0.95 | 0.83 |
| U-16 | 0.90 | 1.31 | 1.69 | 0.78 | 1.30 | 1.58 | 0.88 | 1.08 | 0.83 | 1.27 | 1.24 |
| U-20 | 0.89 | 1.43 | 1.54 | 0.97 | 1.55 | 6.80 | 1.17 | 1.31 | 2.74 | 1.60 | 1.50 |

TABLE 2

| Serum | 14 kDa | MPT63 | MPB70 | MPT51 | MPT59 | 3 kDa | MTC28 | 45/47 kDa | M.tb.CF |
|---|---|---|---|---|---|---|---|---|---|
| Normal | 0.05 | 0.09 | 0.03 | 0.03 | 0.02 | 0.09 | 0.07 | 0.05 | 0.06 |
| No. 602 | 0.40 | 0.41 | 1.15 | 0.22 | 0.52 | 0.88 | 0.94 | 2.21 | 1.54 |
| No. 610 | 0.13 | 0.61 | 0.04 | 0.25 | 0.01 | 0.22 | 0.13 | 0.01 | 0.15 |
| No. 613 | 0.32 | 0.59 | 0.27 | 0.10 | 0.03 | 0.50 | 0.11 | 0.01 | 0.89 |
| No. 614 | 0.23 | 0.37 | 0.13 | 0.40 | 0.28 | 0.52 | 0.77 | 1.76 | 0.62 |
| No. 621 | 0.58 | 0.27 | 0.10 | 0.37 | 0.01 | 0.45 | 0.03 | 0.01 | 0.23 |
| No. 622 | 0.41 | 0.27 | 0.16 | 1.06 | 0.01 | 0.41 | 0.10 | 0.29 | 0.70 |
| No. 628 | 0.29 | 0.51 | 0.12 | 0.44 | 0.02 | 0.58 | 0.21 | 0.41 | 0.50 |
| No. 631 | 0.31 | 0.24 | 0.02 | 0.98 | 0.01 | 0.47 | 0.14 | 0.01 | 0.55 |

For serodiagnosis, this invention includes a cocktail of purified protein or polypeptide antigens specific to the pathogen. For example, a combination of the following three antigens can be used: MTC28, 38 Kda and ESAT-6. As stated, where an entire protein is not specific for M. tuberculosis, it may well contain at least one epitope that is specific. Of the proteins listed in Table 1, 14 Kda, 19 kDa and 45/47 Kda are known to include specific polypeptide sequences.

Several tests were done to show that antigen cocktails of this invention improve both the sensitivity and the specificity of serologic immnoassays. We note that in ELISA the amount of each protein in a combination is only a fraction of the amount of the same protein used alone. Results are presented in Tables 3–6. Table 3 presents ELISA results for IgG antibodies in rabbit and guinea pig immune sera using purified recombinant proteins of M. tuberculosis and, for comparison, M. tuberculosis culture filtrates. Rabbit immune serum was generated against whole culture filtrates of M. tuberculosis and guinea pig sera were obtained from animals aerosol-infected with M. tuberculosis. ELISA plates were coated with either 1 $\mu$g/ml of one of four single proteins (MPT59, 38 kDa, MTC28 and 80 Kda) or 2 $\mu$g/ml of a combination of equal amounts of those four ("combi") or 4 $\mu$g/ml of M. tuberculosis culture filtrates ("M.tb.CF"). Rabbit serum was diluted 1:1000, and guinea pig serum was diluted 1:200. Results are presented as $OD_{405}$ readings. As compared to the use of individual antigens and culture filtrates, detection of IgG antibodies was enhanced using a combination of the four antigens. No increase in non-specific background binding was observed.

TABLE 3

| Serum | MPT59 | 38 kDa | MTC28 | 80 kDa | Combi | M.tb.CF |
|---|---|---|---|---|---|---|
| Rabbit | | | | | | |
| Normal | 0.04 | 0.09 | 0.10 | 0.05 | 0.08 | 0.07 |
| Anti-M.tb. CF. | 0.52 | 0.55 | 0.43 | 0.22 | 0.70 | 0.60 |
| Guinea Pig | | | | | | |
| Normal | 0.04 | 0.13 | 0.08 | 0.07 | 0.10 | 0.06 |
| M.tb. infected | 0.72 | 1.07 | 0.89 | 0.76 | 1.32 | 1.03 |

In a second ELISA test, sera from cattle experimentally infected with M. bovis were assayed for IgM and IgG antibodies using one of three purified antigens of M. tuberculosis (ESAT-6, 14 kDa and MPB70), and a combination of equal amounts of those three and, for comparison, M. bovis culture filtrates ("M.bov.CF"). ELISA plates were coated using 1 $\mu$g/ml of each single antigen or 1.5 $\mu$g/ml of the combination ("Combi") or 4 $\mu$g/ml of M. bov. CF. Sera were diluted 1:100. The results, presented as $OD_{405}$ readings in Table 4, demonstrate that overall sensitivity of the assay using the combination of antigens was in most cases significantly higher than the sensitivity for any antigen separately or for the culture filtrates.

TABLE 4

| Serum | Ig isotype | ESAT-6 | 14 kDa | MPB70 | Combi | M bov.CF |
|---|---|---|---|---|---|---|
| Normal | IgM | 0.10 | 0.16 | 0.14 | 0.15 | 0.06 |
|  | IgG | 0.06 | 0.11 | 0.16 | 0.14 | 0.22 |
| No. 867 | IgM | 0.08 | 0.14 | 0.32 | 0.35 | 0.04 |
|  | IgG | 0.22 | 0.29 | 0.94 | 0.98 | 0.77 |
| No. 868 | IgM | 0.08 | 0.21 | 0.22 | 0.29 | 0.02 |
|  | IgG | 0.42 | 0.45 | 1.56 | 1.51 | 1.25 |
| No. 869a | IgM | 0.24 | 0.27 | 0.51 | 0.60 | 0.15 |
|  | IgG | 1.18 | 0.38 | 0.16 | 1.45 | 0.44 |
| No. 869b | IgM | 0.19 | 0.25 | 0.64 | 0.78 | 0.19 |
|  | IgG | 1.15 | 0.81 | 1.35 | 1.56 | 1.14 |
| No. 872 | IgM | 0.26 | 0.33 | 0.62 | 0.67 | 0.27 |
|  | IgG | 0.21 | 0.81 | 1.60 | 1.68 | 1.16 |
| No. 899 | IgM | 0.09 | 0.15 | 0.54 | 0.42 | 0.15 |
|  | IgG | 0.57 | 0.99 | 1.79 | 1.52 | 1.49 |

In a third ELISA test, sera from patients with active TB were assayed for IgG antibodies using five purified recombinant antigens (MPT63, MPT64, MPT51, 38 kDa and 45/47 kDa) of M. tuberculosis and a combination of equal amounts of those five. ELISA plates were coated using 1 $\mu$g/ml of each single antigen or 2 $\mu$g/ml of the combination ("Combi"). Sera were diluted 1:100. Results are presented as $OD_{405}$ in Table 5. In this human TB serology study, as in the other tests reported above, we observed enhanced detection of specific IgG antibody when combining purified antigens of M. tuberculosis. The magnitude of the enhancing effect was less than that observed with animals, probably due to the generally low levels of the antibody responses in human TB. Use of antigen combinations to increase the sensitivity of serodiagnostic assays in human TB will have particular benefit in HIV-infected TB patients in view of their decreased immune responses.

TABLE 5

| Serum | MPT63 | MPT64 | MPT51 | 38 kDa | 45/47 kDa | Combi |
|---|---|---|---|---|---|---|
| Normal | 0.04 | 0.09 | 0.07 | 0.07 | 0.08 | 0.08 |
| TB-U8 | 0.19 | 0.25 | 0.22 | 0.27 | 0.22 | 0.33 |
| TB-U9 | 0.12 | 0.26 | 0.11 | 0.16 | 0.15 | 0.26 |
| TB-U12 | 0.22 | 0.24 | 0.15 | 0.21 | 0.18 | 0.26 |
| TB-U17 | 0.26 | 0.24 | 0.25 | 0.28 | 0.19 | 0.35 |

In a fourth ELISA test broncho-alveolar lavage ("BAL") fluids obtained from radiologically involved lung lobes of HIV-infected and HIV-negative patients with active pulmonary TB, as well as from an individual with neither ("normal") were assayed for IgG antibodies using one of five recombinant purified proteins of *M. tuberculosis* (MPT63, MPT64, MPT51, 38 kDa and 45/47 kDa) and a combination of equal amounts of those five. ELISA plates were coated using 1 μg/ml of each single antigen or 2 μg/ml of the combination ("Combi"). BAL fluids were obtained from radiologically involved lung lobes of patients with active pulmonary TB and tested at a dilution of 1:5. Results, presented in Table 6, are expressed as $OD_{405}$ values obtained by subtracting sample non-specific binding ($OD_{405}$ test antigen minus $OD_{450}$ BSA (unrelated protein)). Combining the protein antigens for ELISA was superior to using a single purified antigen in the detection of specific antibodies in BAL fluids from TB patients, including HIV-infected TB patients.

cocktails included three antigens specific to the *M. tuberculosis* complex. The three cocktails were all markedly more specific than the PPD preparations.

TABLE 7

| No. | Antigen | Dose (ug/0.1 ml) | Diameter (mm) of area of erythema and induration 24 h after antigen injection in animals immunized with | | Specificity Index |
|---|---|---|---|---|---|
| | | | M Bovis BCG | M.Avium | |
| 1 | MPT63 | 2.0 | 7.5 ± 1.6 | 1.7 ± 1.6 | 4.41 |
| 2 | MPT64 | 2.0 | 7.6 ± 1.0 | Not Determined | — |

TABLE 6

| Patient | TB | HIV | MPT63 | MPT64 | MPT51 | 38 kDa | 45/47 kDa | Combi |
|---|---|---|---|---|---|---|---|---|
| No. 106 (normal) | – | – | <0.01 | <0.01 | <0.01 | <0.01 | <0.01 | 0.01 |
| No. 100 | + | – | 0.09 | 0.07 | 0.14 | 0.22 | 0.27 | 0.33 |
| No. 123 | + | – | 0.07 | 0.01 | 0.09 | 0.16 | 0.16 | 0.28 |
| No. 125 | + | – | 0.19 | 0.10 | 0.13 | 0.09 | 0.01 | 0.24 |
| Nwt | + | + | 0.20 | 0.21 | 0.07 | 0.05 | 0.05 | 0.26 |

PPD is the only commercially available preparation used worldwide for skin test diagnosis of human and bovine TB. PPD is an heterogeneous mixture of antigenically active polypeptides derived from mycobacteria cultured in vitro. Antigen combinations according to this invention comprising a cocktail of purified protein and/or polypeptide antigens, either recombinant or purified from *M. tuberculosis*, that are specific to the *M. tuberculosis* complex are superior to PPD in the overall diagnostic specificity to TB in skin tests. We tested skin reactivity and specificity in guinea pigs immunized with *M. bovis* BCG or with *M. avium* using six purified *M. tuberculosis* antigens (MPT63, MPT64, MTC28, 45/47 Kda MPT51 and 38 kDa), different combinations in equal amounts thereof, *M. bovis* PPD and *M. avium* PPD. Antigens, including PPD control preparations, were injected intradermally five weeks after immunization of guinea pigs with mycobacteria. We note that in these skin tests the amount of a particular antigen in a combination is only a fraction of the amount of that antigen when used singly. Results are reported in Table 7. Specificity is calculated as a specificity index, which is the ratio of the mean obtained in guinea pigs immunized with *M. bovis* BCG to that obtained in *M. avium* immunized animals (specificity index for M. avium PPD is the ratio of the mean obtained in guinea pigs immunized with *M. avium* to that obtained in *M. bovis* BCG-immunized animals). Values above 2.00 were judged to be specific skin reactivity.

Of the antigens used, three were specific and highly reactive in this test (MPT63, MPT64 and MTC28). Another candidate for human skin testing, ESAT-6, was not used in this particular test, only because the gene for it is not present in BCG. One cocktail, Combi-A(1–2) included MPT63 and MPT64. A second cocktail, Combi B(1–4) included those antigens plus MTC28 and 45/47 Kda. A third cocktail, Combi-C(1–6), contained all six antigens. Cocktails of two, four and six purified, recombinant proteins of *M. tuberculosis* demonstrated considerably higher skin test activity than any single antigen, at the same total protein dose (2 μg/0.1 ml) of protein. Skin reactivity to the cocktail of four and six antigens was comparable to reactivity to PPD. Both TABLE 7-continued

| No. | Antigen | Dose (ug/0.1 ml) | Diameter (mm) of area of erythema and induration 24 h after antigen injection in animals immunized with | | Specificity Index |
|---|---|---|---|---|---|
| | | | M Bovis BCG | M.Avium | |
| 3 | MTC28 | 2.0 | 6.6 ± 1.4 | 2.0 ± 1.7 | 3.30 |
| 4 | 45/47 kDa | 2.0 | 7.2 ± 1.3 | 7.2 ± 2.1 | 1.00 |
| 5 | MPT51 | 2.0 | 6.0 ± 0.8 | 5.0 ± 1.2 | 1.20 |
| 6 | 38kDa | 2.0 | 4.3 ± 0.9 | Not Determined | — |
| 7 | Combi-A | 2.0 | 8.8 ± 1.8 | 3.9 ± 0.4 | 2.26 |
| 8 | Combi-B | 2.0 | 10.9 ± 2.2 | 5.2 ± 1.4 | 2.10 |
| 9 | Combi-C | 2.0 | 13.5 ± 2.2 | 5.4 ± 2.0 | 2.50 |
| 10 | M.bovis | 0.2 | 12.1 ± 1.3 | 8.5 ± 1.2 | 1.42 |
| 11 | M.avium | 0.2 | 9.4 ± 1.0 | 12.6 ± 1.4 | 1.34 |

1. Andersen, A. B. and Brennan, P. 1994. Proteins and antigens of *Mycobacterium tuberculosis*. p. 307–327. In B. R. Bloom, (ed). Tuberculosis: pathogenesis, protection and control. ASM Press, Washington, DC.
2. Andersen, B. A. and Hansen, E. B. 1989. Structure and mapping of antigenic domains of protein antigen b, a 38,000-molecular-weight protein of *Mycobacterium tubeiculosis*. Infect. Immun. 57.: 2481–2488.
3. Andersen, P., Askgaard, D., Ljungqvist, L., and Bennedsen, J. 1991. Proteins released from *Mycobacterium tuberculosis* during growth. Infect. Immun. 59: 1905–1910.
4. Andersen, P., Askgaard, D., Ljungqvist, L., Bentzon, M. W., and Heron, I. 1991. T-cell proliferative response to antigens secreted by *Mycobacterium tuberculosis*. Infect. Immun. 59: 1558–1563.
5. Andersen, P. and Heron, I. 1993. Specificity of a protective memory immune response against *Mycobacterium tuberculosis*. Infect. Immun. 61: 844–851.

6. Ashbridge, K. R. A., Booth, R. J., Watson, J. D., and Lathigra, R. B. 1989. Nucleotide sequence of the 19 kDa antigen gene from *Mycobacterium tuberculosis*. Nucl. Acids Res. 17:1249.
7. Bloch, H. and Segal, W. 1955. Viability and multiplication of vaccines in immunization against tuberculosis. Am. Rev. Tubercul. Pulm. Dis. 71: 228–48.
8. Boesen, H., Jensen, B. N., Wilcke, T., and Andersen, P. 1995. Human T-cell responses to secreted antigen fractions of *Mycobacterium tuberculosis*. Infect. Immun. 63: 1491–1497.
9. Borremans, M., Wit, L. d., Volckaert, G., Ooms, J., Bruyn, J. d., Huygen, K., Vooren, P. v., Stelandre, M., Verhofstadt, R., and Content, J. 1989. Cloning, sequence determination and expression of 32-Kilodalton protein gene of *Mycobacterium tuberculosis*. Infect. Immun. 57: 3123–3130.
10. Closs, O., Harboe, M., Axelsen, N. H., Bunch-Christensen, K., and Magnusson, M. 1980. The antigens of *Mycobacterium bovis*, strain BCG, studied by crossed immunoelectrophoresis: a reference system. Scand. J. Immunol. 12: 249–263.
11. Content, J., Cuvellerie, A. d. l., Wit, L. d., Vincent-Levy-Frebault, V., Ooms, J., and Bruyn, J. D. 1991. The genes coding for the antigen 85 complexes of *Mycobacterium tuberculosis* and *Mycobacterium bovis* BCG are member of a gene family: cloning, sequence determination, and genomic organization of the gene coding for antigen 85-C of *M. tuberculosis* 59:3205–3212.
12. Harilw, E. and Lane, D. 1988. Antibodies. A laboratory manual. C:old Spring Harbor Laboratory, Cold Spring Harbor, N.Y.
13. Havlir, D. V., Wallis, R. S., Boom, W. H., Daniel, T. M., Chervenak, K., and Ellner, J. J. 1991. Human immune response to *Mycobacterium tuberculosis* antigens. Infect. Immun. 59: 665–670.
14. Horwitz, M. A., Lee, B.-W. E., Dillon, B. J., and Harth, G. 1995. Protective immunity against tuberculosis induced by vaccination with major extracellular proteins of *Mycobacterium tuberculosis*. Proc. Natl. Acad. Sci. USA 92: 1530–1534.
15. Hubbard, R. D., Flory, C. M., and Collins, F. M. 1992. Immunization of mice with mycobacterial: culture filtrate proteins. Clin. Exp. Immunol. 87: 94–98.
16. Kroll, J. 1983. Tandem crossed immunoelectrophoresis. Scand. J. Immunol. 17, SUPPL. 10.
17. Laqueyrerie, A., Militzer, P., Romain, F., Eiglmeier, K., Cole, S., and Marchal, G. 1995. Cloning, sequencing and expression of the apa gene coding for the *Mycobacterium tuberculosis* 45/47-Kilodalton secreted antigen complex.
19. Matsumoto, S., Matsuo, T., Ohara, N., Hotokezaka, H., Naito, M., Minami, J., and Yamada, T. 1995. Cloning and sequencing of a unique antigen MPT70 from *Mycobacterium tuberculosis* H37Rv and expression in BCG using *E. coli* Mycobacteria shuttle vector. Scand. J. Immunol. 41: 281–287.
20. Matsuo, K., Yamaguchi, R., Yamazaki, A., Tasaka, H., and Yamada, T. 1988. Cloning and expression of the *Mycobacterium bovis* BCG gene for extracellular ~x-antigen. J. Bacteriol. 170: 3847–3854.
21. Nagai, S., Wiker, H. G., Harboe, M., and Kinimoto, M. 1991. Isolation and partial caracterization of major protein antigens in the culture fluid of *Mycobacterium tuberculosis*. Infect. Immun. 59: 372–382.
22. Orme, I. M. 1988. Induction of non specific acquired resistance and delayed-type hypersensitivity, but not specific acquired resistance, in mice inoculated with killed Mycobacterial vaccines. Infect. Immun. 56: 3310–3312.
23. Orme, I. M., Andersen, P., and Boom, W. H. 1993. T cell response to *M. tuberculosis*. J. Infect. Dis. 167: 1481–1497.
24. Ouchterlony, O. 1949. Antigen-antibody reactions in gels. Ark. Chemi. Mineral Geol. 26: 1–5.
25. Qiagen. 1992. The QIAexpressionist. Qiagen Inc., Chatsworth, Calif.
26. Roberts, A. D., Sonnenberg, M. G., Ordway, D. J., Furney, S. K., Brennan, P. J., Belisle, J. T., and Orme, I. M. 1995. Characteristics of protective immunity engendered by vaccination of mice with purified culture filtrate proteins antigens of *Mycobacterium tuberculosis*. Immunology 85: 502–508.
27. Sambrook, J., Fritsch, E. F., and Maniatis, T. 1989. Molecular Cloning. A laboratory Manual. 2nd edition. Cold Spring Harbor Laboratory Press, Cold Spring Harbor, N.Y.
28. Sanger, F., Nicklen, S., and Coulson, A. R. 1977. DNA sequencing with chainterminating inhibitors. Proc. Natl. Acad. Sci. USA 74: 5463–5467.
29. Sorensen, A. L., Nagai, S., Houen, G., Andersen, P., and Andersen, A. B. 1995. Purification and characterization of a low-molecular-mass T-eell antigen secreted by *Mycobacterium tuberculosis*. Infeet. Immun. 63: 1710–1717.
30. Stratagene. 1993. Immunosereening protocol. Stratagene, La Jolla, Calif.
31. Stratagene. 1993. Lambda Zap II Library. A Protocol. Stratagene, La Jolla, calif.
32. Watson, M. E. E. 1984. Compilation of published signal sequences. Nuel. Aeids Res 12:4154–5164.
33. Wiker, H. G., Harboe, M., and Nagai, S. 1991. A localization index for distinction between extracellular and intracellular antigens of *Mycobacterium tuberculosis*. J. Gen. Mierobiol. 137: 875–884.
34. Yamaguehi, R., Matsuo, K., Yamaazaaki, A., Abe, C., Nagai, S., Teresaka, K., and Yamada, T. 1989. Cloning and characterization of the gene for immunogenic protein MPB64 of *Mycobacterium bovis* BCG. Infeet. Immun. 57.: 283–288.
35. Young, D. B., Kaufmann, S. H. E., Hermans, P. W. M., and Thole, J. E. R. 1992. Mycobacterial protein antigens: a compilation. Molec. Microbiol. 6: 133–145.

The invention has been disclosed and described with reference to its preferred embodiments. The test results are provided as examples of the utility of the invention and are not intended to limit the scope of the invention, which will be understood to include derivative DNAs, proteins, polypeptides and vaccines set forth above. In particular, the invention is to be understood to include all modifications within the scope of the appended claims.

We claim:

1. A purified polypeptide, wherein the polypeptide comprises amino acid residues 30 to 159 of SEQ ID NO:2.

2. The polypeptide of claim 1, wherein the polypeptide comprises SEQ ID NO:2.

3. The polypeptide of claim 2, wherein the polypeptide consists of SEQ ID NO:2.

4. A purified polypeptide comprising a fragment of the polypeptide of claim 3, the fragment being shorter than the full-length polypeptide of SEQ ID NO:2 and having antigenic and immunogenic properties.

5. A purified polypeptide fragment of the MTC28 polypeptide (SEQ ID NO:4), the polypeptide fragment being shorter than full-length MTC28 and having antigenic and immunogenic properties.

6. The polypeptide fragment of claim 5, wherein the polypeptide fragment consists of amino acid residues 33 to 310 of SEQ ID NO:4.

7. A composition comprising at least two purified polypeptides of the *Mycobacterium tuberculosis* complex, wherein at least one of the polypeptides is a polypeptide selected from the group consisting of: (a) MPT63 polypeptide (SEQ ID NO:2); (b) a polypeptide comprising amino acid residues 30–159 of SEQ ID NO:2; (c) a fragment of MPT63 polypeptide shorter than full-length MPT63 polypeptide and having antigenic and immunogenic properties; (d) MTC28 polypeptide (SEQ ID NO:4); (e) a polypeptide comprising amino acid residues 33–310 of SEQ ID NO:4; and (f) a fragment of MTC28 polypeptide shorter than full-length MTC28 polypeptide and having antigenic and immunogenic properties.

8. A fusion protein comprising two domains, wherein the first domain comprises:

(a) a MPT63 polypeptide (SEQ ID NO:2); or (b) a fragment of the MPT63 polypeptide shorter than full-length MPT63 polypeptide and having antigenic and immunogenic properties.

9. The fusion protein of claim 8, wherein the second domain comprises a polyhistidine tag.

10. A fusion protein comprising two domains, wherein the first domain comprises:

(a) a MTC28 polypeptide (SEQ ID NO:4); or (b) a fragment of the MTC28 polypeptide shorter than full-length MTC28 polypeptide and having antigenic and immunogenic properties.

11. The fusion protein of claim 10, wherein the second domain comprises a polyhistidine tag.

* * * * *